United States Patent
Ito et al.

(10) Patent No.: US 6,471,868 B1
(45) Date of Patent: *Oct. 29, 2002

(54) METHOD OF PREPARING GLASS FIBER FILTER

(75) Inventors: Toshihisa Ito; Takaki Arai; Kenichiro Yazawa; Osamu Seshimoto, all of Saitama (JP)

(73) Assignee: Fuji Photo Film Co., Ltd., Kanagawa (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/680,179

(22) Filed: Oct. 5, 2000

Related U.S. Application Data

(63) Continuation of application No. 09/287,423, filed on Apr. 7, 1999, now abandoned.

(30) Foreign Application Priority Data

Apr. 10, 1998 (JP) ............................................. 9-099422
Apr. 10, 1998 (JP) ............................................. 9-099424
Nov. 27, 1998 (JP) ............................................. 9-336749

(51) Int. Cl.$^7$ .......................... B01D 61/14; B01D 61/18; B01D 71/04
(52) U.S. Cl. ....................... 210/645; 210/651; 210/767; 436/79; 436/177; 436/178; 422/101; 65/31; 65/472; 501/39
(58) Field of Search ................................ 210/644–646, 210/650, 649, 503, 508, 767, 500.26, 647, 651, 653, 654; 436/177–178, 807, 16; 430/177–178, 79; 422/101; 65/31.429, 472; 501/39

(56) References Cited

U.S. PATENT DOCUMENTS

| | | | | |
|---|---|---|---|---|
| 3,650,721 A | * | 3/1972 | Hammel et al. | |
| 3,734,802 A | * | 5/1973 | Cohen | |
| 4,007,114 A | * | 2/1977 | Ostreicher | |
| 4,046,948 A | * | 9/1977 | Zlochower | |
| 4,477,575 A | * | 10/1984 | Vogel et al. | |
| 4,657,875 A | * | 4/1987 | Nakashima et al. | 216/97 |
| 4,753,776 A | * | 6/1988 | Hillman et al. | |
| 4,810,394 A | * | 3/1989 | Masuda | |
| 4,816,224 A | * | 3/1989 | Vogel et al. | |
| 4,853,001 A | * | 8/1989 | Hammel | |
| 5,118,428 A | * | 6/1992 | Sand et al. | |
| 5,186,843 A | * | 2/1993 | Baumgardner et al. | |
| 5,262,067 A | * | 11/1993 | Wilk et al. | |
| 5,423,989 A | * | 6/1995 | Allen et al. | 210/650 |
| 5,541,115 A | * | 7/1996 | Siegel et al. | |
| 5,876,605 A | * | 3/1999 | Kitajima et al. | 210/650 |
| 5,908,561 A | * | 6/1999 | Palm et al. | |
| 5,979,669 A | * | 11/1999 | Kitajima et al. | 210/455 |
| 6,190,918 B1 | * | 2/2001 | Chu et al. | |

FOREIGN PATENT DOCUMENTS

JP  0785012 A1 * 7/1997

OTHER PUBLICATIONS

Hawley's Condensed Chemical Dictionary (Lewis, Richard Sr., 13$^{th}$ ed., pp. 215 and 274).*
Derwent abstract of EP 785012A, Accession No. 1997–365763.*

* cited by examiner

*Primary Examiner*—Matthew O. Savage
*Assistant Examiner*—Marianne Ocampo
(74) *Attorney, Agent, or Firm*—Reed Smith LLP

(57) ABSTRACT

A method for preparing a plasma or serum sample from a whole blood sample, by contacting a glass fiber filter which contains calcium, sodium or potassium components with an aqueous solution of an organic acid or a mineral acid to elute the calcium, sodium and potassium components in the glass fiber filter into the aqueous solution, separating the aqueous solution from the filter and washing the glass fiber filter with water to remove any residual aqueous solution adhered thereto and then filtering a whole blood sample through the thus treated fiber filter.

8 Claims, No Drawings

METHOD OF PREPARING GLASS FIBER FILTER

CROSS REFERENCE TO RELATED APPLICATIONS

This application claims priority from and is a continuation of prior application Ser. No. 09/287,423 filed Apr. 7, 1999, now abandoned, the contents of which are incorporated herein by reference.

BACKGROUND OF THE INVENTION

This invention relates to a method of preparing a glass fiber filter suitable for the preparation of plasma or serum by filtering whole blood.

The type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and in site inspection, because of requiring a centrifuge and electricity. Thereupon, it has been investigated to separate plasma or serum from whole blood by filtration.

Several filtration methods using glass fiber filter have been developed wherein whole blood is charged into the glass fiber filter put in a column from one side of the column, and pressurized or evacuated to obtain plasma or serum from the other side (Japanese Patent KOKOKU Nos. 44-14673, 5-52463, Japanese Patent KOKAI Nos. 2-208565, 4-208856).

However, practical filtration methods capable of obtaining an amount of plasma or serum from whole blood necessary for measuring by an automatic analyzer have not been developed except a part of items, such as blood sugar.

On the other hand, the inventors developed a blood filter unit composed of a filter holder and a syringe. The filter holder is composed of a holder body which contains filter material and a cap which is screwed on the holder body. The filter material consists of, e.g. two sheets of glass fiber filter, one sheet of cellulose filter and one sheet of polysulfone microporous membrane (FIG. 1 of EP 785430 A1)

Another blood filter unit composed of a holder body and a cap was also developed. The holder body consists of a plasma receiver located on the upper side and a filter chamber located on the underside. The filter material put in the filter chamber is composed of six sheets of glass fiber filter and one sheet of polysulfone microporous membrane (Example 1 of EP 785012A1).

Incidentally, the electrolytes to be measured for clinical assay include calcium, sodium, potassium, chlorine and so on. However, as a result of investigating commercial glass fiber filters, the inventors found that some of them are eluted into blood to cause analytical errors.

SUMMARY OF THE INVENTION

An object of the invention is to provide a method of preparing a glass fiber filter which does not influence blood component analysis, such as calcium, sodium, potassium and chlorine, even when using for blood filtration.

The inventors investigated in order to solve the above problems, and first, they attempted to wash glass fiber filter with purified water by ion-exchange resins. As a result, sodium was removed by the washing with water, but calcium and potassium were increased conversely. Thereupon, they further investigated, and found that organic acid, mineral acid and hot water are very effective for the removal of calcium, sodium, potassium and so on, to succeed in obtaining a glass fiber filter which has solved the problem of errors caused by these ions.

Thus, the present invention provides a method of preparing a glass fiber filter of which the elution quantity of calcium, sodium and potassium is small, which comprises treating the filter with an organic acid, mineral acid or hot water.

DETAILED DESCRIPTION OF THE INVENTION

Preferable glass fiber filter has a density of about 0.02 to 0.5 g/cm$^3$, preferably about 0.03 to 0.2 g/cm$^3$, more preferably about 0.05 to 0.13 g/cm$^3$, a retainable particle size of about 0.6 to 9 $\mu$m m preferably 1 to 5 $\mu$m.

As an indicator corresponding to v6id volume or filtrate volume of plasma, water permeation speed is suitable. The water permeation speed is determined by putting a glass fiber filter with a definite area in a closed filter unit of which the inlet and outlet can be connected by a tube, adding a definite volume of water, and pressurizing or sucking at a constant pressure. The water permeation speed is filtrate volume per unite area and time, and expressed by ml/sec.

For example, glass fiber filter 20 mm $\phi$ in diameter is put in a filter unit, and a 100 ml syringe containing 60 ml water is connected to the top of the filter unit. Water flows down naturally, and volume of water passing through the glass filter from 10 sec to 40 sec after starting is measured as the water permeation volume, and the water permeation speed per unit area is calculated from it.

Glass fiber filters particularly suitable for plasma or serum separation have a water permeation speed of about 1.0 to 1.3 ml/sec, and illustrative of the glass fiber filters are Whatman GF/D, Toyo Roshi GA-100, GA-200 and the like. Furthermore, the glass fiber filter can be prepared by suspending glass fibers of a commercial glass fiber filter in hot water, and then making the glass fibers into a low density sheet (density: about 0.03 g/cm$^3$) on a nylon net. The glass fiber filter thus prepared shows good plasma separating ability.

A suitable thickness of the glass fiber filter is about 0.1 to 10 mm, preferably about 0.3 to 8 mm.

Suitable organic acids are various carboxylic acids, amino acids and the like, such as acetic acid, citric acid, succinic acid, malic acid, maleic acid and ethylenediaminetetraacetic acid, and particularly, acetic acid is preferable. A suitable concentration of the organic acid is about 0.1 $\mu$M to 1 M, preferably about 1 $\mu$M to 100 mM, particularly preferably 10 $\mu$M to 10 mM. The diluent for adjusting the concentration as above is usually water, and the organic acid used in the invention is usually an aqueous solution.

Suitable mineral acids are hydrochloric acid, nitric acid, sulfuric acid and the like, and a suitable concentration of the mineral acid is about 0.1 $\mu$m to 10 mM, preferably about 0.01 to 0.5 mM. When the concentration of the mineral acid exceeds 10 mM, the analytical values of potassium and calcium become to low. The diluent for adjusting the concentration as above is also usually water, and the mineral acid is usually an aqueous solution.

The treatment of the glass fiber with the organic acid or mineral acid is carried out by contacting the glass fiber filter with the organic acid or mineral acid, such as immersing or showering, if necessary with moderate stirring or circulating. Suitable treating conditions are, in the case of the organic acid, at 5 to 80° C., preferably for 10 to 60° C. for 1 second to 60 minutes, preferably for 10 seconds to 20 minutes, and in the case of the mineral acid, at 5 to 80° C., preferably at 10 to 60° C., for 1 second to 60 minutes, preferably 0.5 to 20 minutes. A suitable quantity of the organic acid or mineral acid is about 0.1 to 50 l, preferably about 0.2 to 10 l per 10 g glass fiber. During treating, the acid is preferably exchanged once to several times.

After the treatment with the acid, the glass fiber filter is washed with water to remove adhered materials to the glass fiber filter such as the acid. The water for washing is purified water not containing calcium, sodium, potassium and the like at least up to the degree influencing analysis, and demineralized water, such as purified by ion-exchange resins, distilled water or the like is used. The temperature of washing water is about 5 to 80° C., usually ordinary temperature.

When glass fiber filter is treated with hot water, purified water is used as the hot water. The purified water does not contain calcium, sodium, potassium at least up to the degree influencing analysis, and demineralized water, such as purified by ion-exchange resins, distilled water or the like is used.

The treatment of the glass fiber filter with the hot water is also carried out by contacting the glass fiber filter with the hot water, such as immersing or showering, if necessary with moderate stirring or circulating. Suitable treating conditions with the hot water are at about 35 to 100° C., preferably at about 60 to 100° C., for about 1 second to 60 minutes, preferably for about 0.5 to 20 minutes. A suitable quantity of the hot water is about 0. 1 to 50 l, preferably about 0.2 to 10 l per 10 g glass fiber. During treating, the hot water is preferably exchanged once to several times.

After the treatment, it is preferably to replace the washing water remaining in the glass fiber filter by a water-miscible organic solvent, such as acetone or alcohol.

Irrespective of the organic acid, the mineral acid or the hot water, it is preferable to conduct the treatment to the degree of the elution of calcium of 10 mg/l or less, preferably 1 mg/l, the elution of sodium of 400 mg/l or less, preferably 40 mg/l or less, the elution of potassium of 40 mg/l or less, preferably 4 mg/l or less, and except for hydrochloric acid, the elution of chlorine of 600 mg/l or less, preferably 60 mg/l or less, by immersing the treated glass fiber filter in water at ordinary temperature (20° C.) for 60 minutes.

On the other hand, it is also effective that each elution of calcium, sodium, potassium and the like has been measured as to the glass fiber filter to be used, and analytical values are corrected by substracting the elution.

EXAMPLES

Example 1

The glass fiber filter ("GF/D", Whatman) subjected to the treatment had a thickness of 1 mm and a density of 0.10.

The glass fiber filter was cut into circular pieces 9 mm in diameter (weight: 0.778 g), and immersed in each 50 ml of 0.01 mM, 1 mM or 10 mM acetic acid aqueous solution for 30 seconds. The glass fiber filter treated with acetic acid was put in a Buchner funnel, and sucked to remove acetic acid followed by washing with 300 ml water purified by a Millipore membrane. After sucking to remove water, the glass fiber filter was immersed by in 40 ml acetone, and acetone was removed sucking using the Buchner funnel. Then, the glass fiber filter was dried naturally by leaving it.

Blood was filtered by the glass fiber filter thus prepared to obtain plasma, and sodium, potassium, chlorine and calcium of the plasma were analyzed. For comparison, the same blood was filtered by the same glass fiber filter which was untreated or washed merely with water or centrifuged to obtain plasmas, and the plasmas were analyzed. The results are summarized in Table 1.

TABLE 1

| Treatment | Na (meq/L) | K (meq/L) | Cl (meq/L) | Ca (mg/dl) |
|---|---|---|---|---|
| 0.01 mM Acetic Acid | 141.0 | 3.52 | 106.7 | 8.75 |
| 1 mM Acetic Acid | 141.2 | 3.54 | 107.4 | 8.85 |
| 10 mM Acetic Acid | 141.0 | 3.47 | 108.5 | 8.83 |
| Untreated | 146.2 | 3.63 | 112.9 | 8.75 |
| Water | 141.1 | 3.8 | 108.0 | 9.10 |
| Centrifuged | 141.3 | 3.63 | 107.7 | 8.70 |

Analytical Method

Ca: Fuji Dri-Chem Analyzer 5500

Na, K, Cl: Fuji Dri-Chem Analyzer 800

Example 2

The glass fiber filter ("GF/D", Whatman) subjected to the treatment had a thickness of 1 mm and a density of 0. 10.

The glass fiber filter was cut into circular pieces 9 mm in diameter (weight: 0.78 g), and immersed in each 50 ml of 10 mM hydrochloric acid or 10 mM sulfuric aicd for 30 seconds. The glass fiber filter treated with acetic acid was put in a Buchner funnel, and sucked to remove the acid followed by washing with 300 ml water purified by a Millipore pure water manufacturing apparatus ("Milli Q"). After sucking to remove water, the glass fiber filter was immersed by in 40 ml acetone, and acetone was removed sucking using the Buchner funnel. Then, the glass fiber filter was dried naturally by leaving it.

Blood was filtered by the glass fiber filter thus prepared to obtain plasma, and sodium, potassium, chlorine and calcium of the plasma were analyzed. For comparison, the same blood was filtered by the same glass fiber filter which was untreated or washed merely with water or centrifuged to obtain plasmas, and the plasmas were analyzed. The results are summarized in Table 2.

TABLE 2

| Treatment | Na (mEq/L) | K (mEq/L) | Cl (mEq/L) | Ca (mg/dl) |
|---|---|---|---|---|
| 10 mM HCl | 142.5 | 3.49 | 106.6 | 8.82 |
| 10 mM $H_2SO_4$ | 141.8 | 3.56 | 107.1 | 8.87 |
| Untreated | 145.3 | 3.94 | 111.9 | 9.00 |
| Water | 142.7 | 4.03 | 107.9 | 9.22 |
| Centrifuged | 142.6 | 3.91 | 107.3 | 8.90 |

Analytical Method

Ca: Fuji Dri-Chem Analyzer 5500

Na, K, Cl: Fuji Dri-Chem Analyzer 800

Example 3

Varying concentration of hydrochloric acid to 0.01 mM, 0.05 mM and 1.0 mM, the same glass fiber filter was treated and evaluated similar to Example 2. The results are summarized in Table 3.

TABLE 3

| Treatment | Na (mEq/L) | K (mEq/L) | Cl (mEq/L) | Ca (mg/dl) |
|---|---|---|---|---|
| 0.01 mM HCl | 143.3 | 4.02 | 107.8 | 9.19 |
| 0.5 mM $H_2SO_4$ | 142.0 | 3.80 | 107.3 | 8.96 |
| 1.0 mM $H_2SO_4$ | 141.9 | 3.69 | 107.6 | 8.90 |
| Untreated | 145.3 | 3.94 | 111.9 | 9.00 |
| Water | 142.7 | 4.03 | 107.9 | 9.22 |
| Centrifuged | 142.6 | 3.91 | 107.3 | 8.90 |

Example 4

0.5 g of glass fiber filter ("GA-100", Advantec) was immersed in 400 ml of 20 mM hydrochloric acid, and extracted at 27° C. or 60° C. for 5 minutes. After returning to ordinary temperature, the glass fiber filter was filtered, and washed three times with distilled water.

Using the glass fiber filter thus obtained, blood was filtered, and the following volume of plasma was obtained.

TABLE 4

| Treatment | Filter Density (g/cm$^2$) | Plasma Volume (µl) |
|---|---|---|
| Untreated | 0.096 | 260 |
| 20 mM · HCl/27° C. | 0.083 | 300 |
| 20 mM · HCl/60° C. | 0.079 | 300 |

Calcium, sodium and potassium of each plasma were analyzed. The plasma obtained by centrifuging was also analyzed. The results are shown in Table 5.

TABLE 5

| Filter | Treatment | Ca | Na | K |
|---|---|---|---|---|
| GA-100 | Untreated | 14.4 | 174 | 4.4 |
|  | 20 mM · HCl/27° C. | 10.9 | 144 | 4.6 |
|  | 20 mM · HCl/60° C. | 10.0 | 141 | 4.2 |
| — | Centrifuged | 9.7 | 140 | 3.9 |

Analytical Method

Ca: Hitachi Analyzer 7150

Na, K: Fuji Dri-Chem Analyzer 800

Example 5

1 g of glass fiber filter ("GF/D", Whatman) was put in 50 ml pure water at 100° C., and refluxed for 15 minutes. After cooling, the glass fibers were filtered by quantitative filter paper, and the filtrate was analyzed.

For comparison, 1 g of the same glass fiber paper ws put in 50 ml pure water, and shaken at ordinary temperature for 15 minutes. The glass fiber filter was filtered by quantitative filter paper, and the filtrate was analyzed.

The results are shown below.

|  | Ca (µg/GF1g) | Na (µg/GF1g) | K (µg/GF1g) | Zn (µg/GF1g) |
|---|---|---|---|---|
| Hot Water Extraction | 138 | 956 | 129 | 24.4 |
| Water Extraction | 5.2 | 585 | 70 | 8.6 |

Analitical Method:

Ca:JIS.K.0102 50.3 ICP Emission Spectral Analysis

Na:JIS.K.0102 48.2 Flame Atomic Absorption Spectrophotometry

K: JIS.K.0102 49.2 Flame Atomic Absorption Spectrophotometry

Zn: JIS.K.0102 53.3 ICP Emission Spectral Analysis

Example 6

About 14 g glass fiber filter ("GF/D", Whatman) was placed on a wire gauze, and immersed in 300 ml purified water at about 70° C. After 5 minutes, the glass fiber filter was taken out, and cooled to room temperature. The glass fiber filter was immersed in about 300 ml acetone to substitute water, and dried by blowing warm air using a dryer. Blood filter units were prepared using the glass fiber filter thus obtained or untreated glass fiber filter, and blood was filtered. Each plasma obtained by the filtration or centrifuging the same blood was analyzed as to sodium ion and chlorine ion by a Hitachi analyzer 7150, and the results are shown below.

|  | Sodium meq/L | Chlorine meq/L |
|---|---|---|
| Untreated | 146.8 | 109.4 |
| Hot Water Extraction | 142.0 | 104.9 |
| Centrifuged | 142.2 | 104.0 |

It can be seen from the results that the plasma obtained using the glass fiber filter treated with hot water can bring similar analytical results to the plasma obtained by centrifuging.

What is claimed is:

1. A method for preparing a plasma or serum sample from a whole blood sample comprising contacting a glass fiber filter containing calcium, sodium and potassium components with an aqueous solution of a compound capable of eluting calcium, sodium and potassium components from the glass fiber filter, said compound being selected from the group consisting of 0.1 µM to 1M of an organic acid and 0.1 µM to 10 mM of a mineral acid, the contacting being carried out for from 1 second to 60 minutes to elute the calcium, sodium and potassium components in the glass fiber filter into the aqueous solution of the compound, separating the aqueous solution from the glass fiber filter and washing the glass fiber filter with water to remove any residual aqueous solution adhered to the glass fiber filter and then filtering the whole blood sample through the thus treated glass fiber filter.

2. The method of claim 1 wherein the compound is an organic acid.

3. The method of claim 2 wherein the organic acid is an aqueous carboxylic acid or amino acid solution.

4. The method of claim 2 wherein the organic acid is an aqueous acetic acid solution.

5. The method of claim 1 wherein the compound is a mineral acid.

6. The method of claim 5 wherein the mineral acid is selected from the group consisting of hydrochloric acid, nitric acid and sulfuric acid.

7. The method of claim 1 wherein the contacting is carried out at 5 to 80° C. for 0.5 to 60 minutes.

8. The method of claim 1 wherein the contacting is carried out to the degree of the elution of calcium of 10 mg/l or less, the elution of sodium of 400 mg/l or less and the elution of potassium of 40 mg/l or less.

* * * * *